United States Patent
Fruchey et al.

(10) Patent No.: US 9,573,874 B2
(45) Date of Patent: Feb. 21, 2017

(54) ACRYLIC ACID AND ACRYLATE ESTER FROM LACTIDE PROCESS

(71) Applicant: SGA POLYMERS, LLC, South Charleston, WV (US)

(72) Inventors: Olan Stanley Fruchey, Hurricane, WV (US); Thomas A. Maliszewski, Charleston, WV (US); John E. Sawyer, Charleston, WV (US)

(73) Assignee: SGA Polymers, LLC, South Charleston, WV (US)

( * ) Notice: Subject to any disclaimer, the term of this patent is extended or adjusted under 35 U.S.C. 154(b) by 0 days.

(21) Appl. No.: 14/785,353

(22) PCT Filed: Apr. 17, 2014

(86) PCT No.: PCT/US2014/034496
§ 371 (c)(1),
(2) Date: Oct. 19, 2015

(87) PCT Pub. No.: WO2014/172540
PCT Pub. Date: Oct. 23, 2014

(65) Prior Publication Data
US 2016/0083323 A1      Mar. 24, 2016

Related U.S. Application Data

(60) Provisional application No. 61/813,926, filed on Apr. 19, 2013.

(51) Int. Cl.
C07C 67/30    (2006.01)
C07C 51/09    (2006.01)
C07C 67/10    (2006.01)
C07C 67/327   (2006.01)
C07C 67/02    (2006.01)

(52) U.S. Cl.
CPC .............. *C07C 51/09* (2013.01); *C07C 67/02* (2013.01); *C07C 67/10* (2013.01); *C07C 67/327* (2013.01)

(58) Field of Classification Search
CPC ............ C07C 67/10; C07C 51/43; B01J 35/02
USPC ........................................... 560/211
See application file for complete search history.

(56) References Cited

U.S. PATENT DOCUMENTS

2008/0119374 A1* 5/2008 Willberg ............... C09K 8/52
507/209
2012/0078004 A1* 3/2012 Fruchey ................ C07C 67/08
560/211

OTHER PUBLICATIONS

International Search Report (PCT/US2014/034496), Oct. 13, 2014.*
International Preliminary Report on Patentability, issued on Oct. 29, 2015 in original PCT application PCT/US2014/034496.

* cited by examiner

*Primary Examiner* — Kofi Adzamli
(74) *Attorney, Agent, or Firm* — Dinsmore & Shoh LLP; Monika L'orsa Jaensson, Esq.

(57) ABSTRACT

Technical grade acrylic acid derived from renewable resources utilizing a base catalyst system by a process including reacting lactide (or lactic acid oligomers) with methyl acetate to form methyl 2-acetoxypropionate in the presence of a base catalyst such as sodium methoxide, pyrolyzing the methyl 2-acetoxypropionate, with or without a catalyst, to methyl acrylate and acetic acid, transesterifying the mixture to acrylic acid and methyl acetate, separating and purifying the acrylic acid by distillation late in the presence of polymerization inhibitor(s). The disclosed process will produce a "green" (i.e. renewable resources derived) acrylic acid and/or methyl acrylate ester.

12 Claims, 3 Drawing Sheets

ACRYLIC ACID AND ACRYLATE ESTER FROM LACTIDE PROCESS

CROSS-REFERENCE TO RELATED APPLICATIONS

Figure 1:
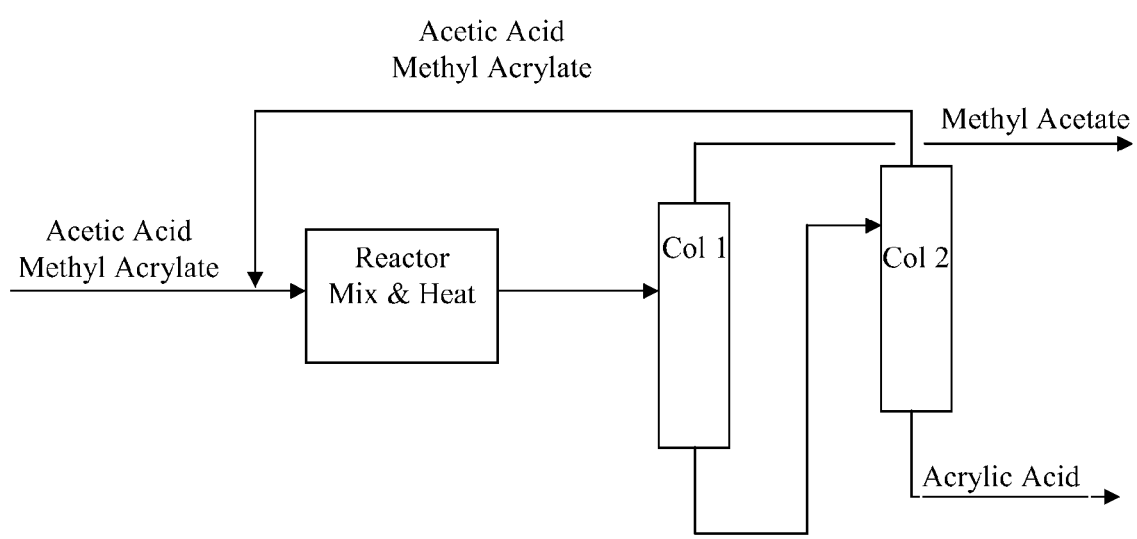

This application claims priority to U.S. Provisional Application Ser. No. 61/813,926, filed Apr. 19, 2013 which is incorporated by reference herein in its entirety The present invention is generally directed toward a process to create acrylic acid and methyl acrylate. More specifically, the present invention is directed toward a process to create technical grade acrylic acid or/and methyl acrylate ester from renewable resources.

For purposes of this invention, the term green technical grade acrylic acid or green acrylic acid refers to technical grade acrylic acid derived from renewable resources.

BACKGROUND

The acrylic acid market is measured by the production of crude acrylic acid. Crude acrylic acid (also known as technical grade acrylic acid) is not an item of commerce. However, it is either further purified into glacial acrylic acid or converted into Acrylate esters. The market is equally split between glacial and ester production (i.e. 50% of the crude goes to glacial and 50% goes to esters). The worldwide capacity for crude acrylic acid has been estimated at over 9 billion pounds per year.

All current production of crude acrylic acid is via a two stage air oxidation of propylene. In the first stage propylene is oxidized to acrolein using an expensive Bi/Mo based mixed metal oxide catalyst. In the second stage the acrolein is oxidized to acrylic acid using an expensive Bi/V based mixed metal oxide catalyst. Both oxidation steps are conducted at high temperature (320° C. and 280° C., respectively) in very expensive shell and tube reactors using molten salt heat exchange fluids.

The hot gases exiting the second reactor are rapidly cooled and the non-condensables are separated from the condensed aqueous acrylic acid solution in the absorber. The concentration of the acrylic acid in this aqueous solution depends on the technology employed. One technology uses steam injection into the reactors to control flammability and the other uses recycle gas injection instead of steam. Steam injection can lead to an aqueous acrylic acid solution as low as ~20% while recycle gas injection can produce an aqueous acrylic acid as high as 70% leaving the absorber.

This aqueous acrylic acid is then subjected to a complicated purification system consisting of several towers to produce crude acrylic acid (technical grade). In the first tower water is removed. If steam was used as the diluent in the reactors the water is removed via extraction and azeotropic distillation is used if recycle gas was employed. In both cases the dewatered acrylic acid is then subjected to multiple vacuum distillations to remove both light and heavy by-products. The final product from these distillation steps is technical grade acrylic acid (>99% purity).

The capital cost for a crude acrylic acid unit is very high. Furthermore, the high raw material cost of propylene makes it vulnerable to a new technology for some of the future Acrylic acid production units.

Currently, there is no commercially viable micro-organism which can directly produce acrylic acid via fermentation. However, there are known micro-organisms which can produce specific hydroxypropionic acids (acrylic acid precursors) via glucose fermentation. There are two configurational isomers of hydroxypropionic acid. The alpha isomer is commonly known as lactic acid and the beta isomer is better known a 3-hydroxypropionic acid (3HPA). Lactic acid has been produced on a commercial scale via fermentation for over one hundred years while 3HPA is not yet commercially available.

Both isomers undergo acid catalyzed dehydration yielding acrylic acid, see Chemical Reaction 1:

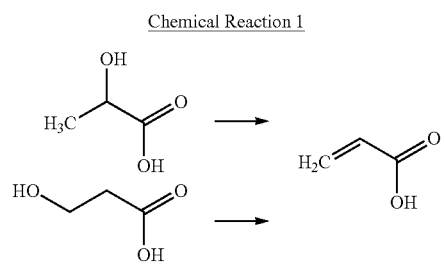

Chemical Reaction 1

However, the two isomers yield different amounts of acrylic acid. The beta isomer (3HPA) dehydrates in near quantitative yields while the alpha isomer (lactic acid) only realizes ~55% yield. These dehydration efficiencies are essentially the same for both the free acids and the corresponding lactate esters. The reason for this difference in selectivity to acrylic acid is most likely related to the location of the intermediate carbocation. Lactic acid proceeds through a carbocation alpha to the carbonyl (which can readily undergo decomposition) and 3HPA proceeds through a carbocation beta to the carbonyl (i.e. the positive charge is removed from the carbonyl and can only readily eliminate a proton forming acrylic acid).

While the dehydration of lactic acid to acrylic acid has been studied for over 50 years, the yield remains poor. This poor dehydration efficiency is also observed for lactate esters. However, it has been shown that the acetylated product of methyl lactate (methyl 2-acetoxypropionate) readily undergoes pyrolysis to methyl acrylate in ~90% yields (see Chemical Reaction 2). Somewhat lower yields of acrylic acid have also been reported for the pyrolysis of 2-acetoxypropionic acid.

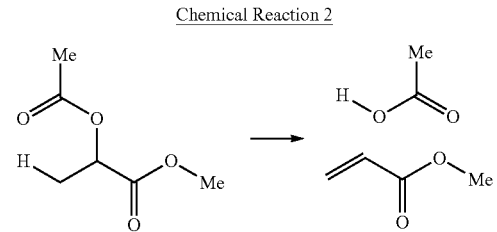

Chemical Reaction 2

This pyrolysis reaction is a cyclic elimination of acetic acid and goes in high yields because it does not proceed through the carbocation intermediate associated with the dehydration of methyl lactate. Obviously lactic acid could be converted into one of these acetoxy derivatives and then pyrolyzed to produce acrylic acid or methyl acrylate. The problem with this route is that the acetoxy derivative would be typically made by reaction of lactic acid or methyl lactate with either acetic anhydride or ketene. The recovered acetic acid could be converted back to anhydride or ketene using a ketene furnace, but a ketene furnace is very expensive.

Furthermore, the lactic acid is only available as an aqueous solution so excess ketene or anhydride would be consumed by the water present in the aqueous lactic acid further decreasing the economic viability of this route. To utilize this route via the acetoxy derivative one must be able to prepare it directly from acetic acid.

Thus, there is a need for a more effective and efficient process to create acrylic acid and methyl acrylate ester.

BRIEF SUMMARY OF THE INVENTION

The present invention satisfies the needs discussed above. The present invention is generally directed toward a process to create acrylic acid. More specifically, the present invention is directed toward a process to create technical grade acrylic acid from renewable resources.

It is to be understood that the invention is not limited in its application to the details of the construction and arrangement of parts illustrated in the accompanying drawings. The invention is capable of other embodiments and of being practiced or carried out in a variety of ways. It is to be understood that the phraseology and terminology employed herein are for the purpose of description and not of limitation.

One aspect of the present invention discloses the use of base catalyst systems (e.g. sodium methoxide, potassium methoxide, sodium hydroxide, potassium hydroxide, sodium acetate or potassium acetate) with lactide (or other oligomers of lactic acid) and methyl acetate to achieve high conversions to methyl 2-acetoxypropionate. After the contents are subjected to pyrolyzation, a mixture of methyl acrylate and acetic acid is obtained. This mixture can be transesterified to an equilibrium mixture of acrylic acid, acetic acid, methyl acetate, and methyl acrylate. After distillation, the resulting semi-purified acrylic acid would be a technical grade acrylic acid, and the methyl acetate returns to the first reaction. The methyl acrylate and acetic acid can be recycled to the transesterification or some of the methyl acrylate can be taken as a product.

Upon reading the above description, various alternative embodiments will become obvious to those skilled in the art. These embodiments are to be considered within the scope and spirit of the subject invention, which is only to be limited by the claims which follow and their equivalents.

DESCRIPTION OF THE INVENTION

The present invention satisfies the needs discussed above. The present invention is generally directed toward a process to create acrylic acid. More specifically, the present invention is directed toward a process to create technical grade acrylic acid from renewable resources.

Green acrylic acid and acrylate products are prepared from fermentation derived lactic acid. Lactide (anhydrous solid) is currently produced commercially from aqueous lactic acid and used as the monomer for the production of polylactic acid.

The present invention discloses the use of a base catalyst at high temperature (~240° C.). The base catalyst can be sodium methoxide (or any alkali methoxide), or sodium hydroxide (or any alkali hydroxide) or sodium acetate (or any alkali acetate). These catalysts have been shown to convert lactide and methyl acetate into methyl 2-acetoxypropionate. This same reaction can be applied to any relatively anhydrous oligomer or polymer of lactic acid. In other words, lactide (the cyclic dimer of lactic acid) is only one of several possible feeds for the envisioned process.

The acrylic acid unit of the present invention consists of a reaction step in which lactide (or lactic acid oligomer) is reacted with methyl acetate in the presence of sodium methoxide (or potassium methoxide, or sodium hydroxide, or potassium hydroxide, or sodium acetate, or potassium acetate) catalyst forming methyl 2-acetoxypropionate. The methyl 2-acetoxypropionate would then be separated and pyrolyzed to methyl acrylate and acetic acid. This pyrolysis can be done either with or without a catalyst. One possible catalyst for the pyrolysis step would be calcium sulfate. Additional catalysts include zeolites such as ultrastable y-type zeolite (USY), mordenite, Hydrophobic Zeoloite Socony Mobil number 5 (H-ZSM 5), an X zeolite, beta zeolite, or Sn-beta zeolite; mesoporous molecular sieves such as Mobil Composition of Matter number 41 (MCM-41); naturally occurring acidic clays such as montmorillonite or kaolinite; an acidic metal oxide such as alumina, tin (IV) oxide, molybdenum oxide; acidic non-metal oxides such as silica or phosphorous pentoxide; an acidic doped metal oxide such as sulfated zirconia, tungstated zirconia, sulfonated silica, tungstated tin oxide, W—Nb mixed-oxides; a Lewis acid such as FeCl3, AlCl3, ScCl3, or other transition metal salt of a mineral acid; hetero-poly acids such as tungstosilicic acid, molybdosilicic acid, tungstophosphoric acid, and molybdophosphoric acid; or a support doped with one of the foregoing classes of acidic catalysts and combinations and mixtures thereof. All of the foregoing catalysts may be supported on standard catalytic supports for catalysts such as a monolithic structure (as is commonly used in the automotive catalyst industry to support the exhaust catalysts), beaded or pelleted supports, and other structured supports like structured packings. The catalytic material may be used to make the entire support structure, or the catalyst may be added to the surface of an inert support structure by the standard techniques of washcoating or solution impregnation. Suitable inert supports for the monolithic structure or pellets or beads include cordierite, alumina, titania, zirconia, metals such as steel, silica, silicon carbide, boron nitride, silicon nitride, and other inert heat resistant materials.

The effluent from this pyrolysis reactor will be condensed and sent to a transesterification Reactor, with a residence time of 30 minutes to 2 hours. The transesterification Reactor will be warm and will have a transesterification catalyst. The transesterification catalyst can either be a liquid or solid. Possible liquid catalysts would be mineral acids such as sulfuric acid or phosphoric acid. Other possible liquid catalyst would be organic sulfonic acids such as methane sulfonic acid or dodecylbenzene sulfonic acid. Possible solid catalyst would be polymeric sulfonic acids like Amberlyst 30 or Marathon C.

The Reactor is fed methyl acrylate and acetic acid from the pyrolysis step. Transesterification occurs in this reactor. One possible version of this reactor is a fixed bed reactor where the tubes are filled with Amberlyst 30 resin. Given enough time (about 30 minutes to 2 hours, depending on temperature and catalyst) the reaction will achieve an equilibrium distribution.

This transesterification reaction leads to acrylic acid production by converting the methyl acrylate to the desired acrylic acid which is now ready for further refining and transesterifying reactant acetic acid has regenerate methyl acetate for use in the preparation of methyl 2-acetoxypropionate. This allows for methyl acetate to be recovered without azeotropes or other close boiling materials. Thus, the transesterification is accomplished without the complications of water (see FIG. 1).

The methyl acetate would be recovered as the overhead stream of the first distillation tower after the transesterification reaction. If desired the overhead could be a mixture of methyl acetate and methyl acrylate which could then be separated in a subsequent distillation step. In other words the methyl acetate is recycled to the process and methyl acrylate is recovered for further refining and sales. The acrylic acid would be recovered for further purification as the bottom stream of the second distillation column. The overhead could be either pure acetic acid or a mixture of acetic acid and methyl acrylate that would be sent back to the transesterification reactor for recycle. In other words the present invention would allow the production of acrylic acid alone in one embodiment or both acrylic acid and methyl acrylate in another embodiment.

This transesterification reaction could also be performed via reactive distillation. The mixture of methyl acrylate and acetic acid along with a liquid catalyst would be fed to the middle section of a distillation tower while methyl acetate would be taken as the distillate stream and acrylic acid as the residue stream from the tower. The liquid catalyst would be those previously mentioned. Alternatively, a solid acid catalyst could be incorporated in the tower packing.

The distillation steps involving acrylic acid and methyl acrylate would be done in the presence of polymerization inhibitors (e.g. phenothiazine, hydroquinone, p-methoxyphenol, 4-hydroxy TEMPO, etc.). The semi-purified acrylic acid from the distillation steps would be a technical grade acrylic acid which could be optionally further purified to glacial acrylic acid by melt crystallization or reacted with a C-1 to C-8 alcohol to produce an acrylate ester. The glacial acrylic acid product would be stabilized by the addition of 200 ppm of MeHQ for commercial sales and the purified acrylate ester would be stabilized with 15 ppm of MeHQ.

Figure 2:
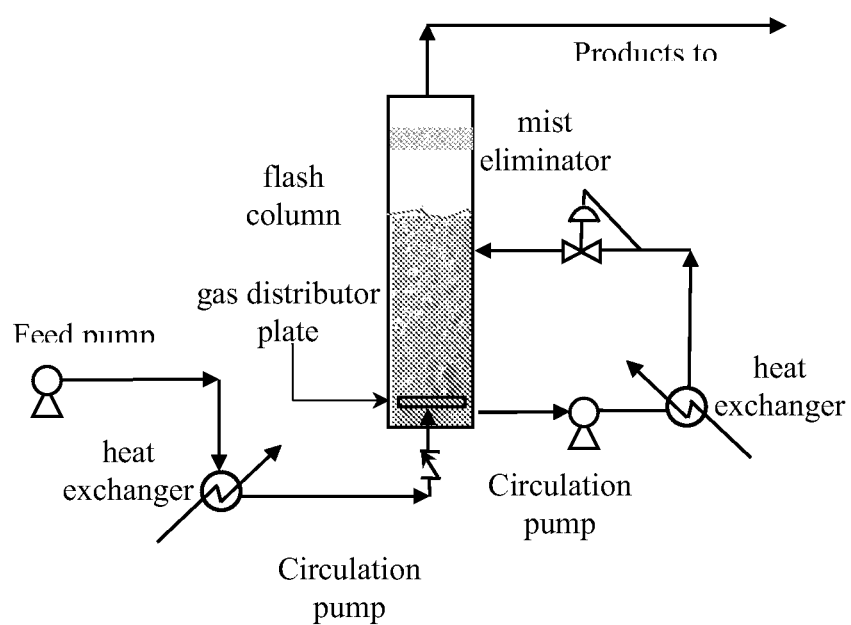

The literature pyrolysis of methyl 2-acetoxypropionate is typically performed at temperatures between 400° C. and 600° C. over a catalytic surface such as calcium sulfate or quartz. The typical reaction is performed by passing gaseous methyl 2-acetoxypropionate through a heated tube which is packed with the catalytic surface. The novel cracking process which is disclosed here accomplishes the pyrolysis in a column filled with high boiling liquid (see FIG. 2 below). The feed boiler consists of a pump and heat exchanger and a check valve which injects hot methyl 2-acetoxypropionate solution into the column. The methyl 2-acetoxypropionate is injected into this column at a temperature near the boiling point. The unreacted high boiling residue in the column may be removed either from the top of the liquid in the column, or from the bottom, depending on the density of the liquid phases in the column. The heat transfer medium is a high boiling liquid that does not flash under the column conditions. The high boiling liquid may or may not contain a homogenous catalyst. When the methyl 2-acetoxypropionate is injected into this hot (~180° C. or higher) high boiling liquid it cracks into methyl acrylate and acetic acid. The volatile methyl acrylate and acetic acid are flashed off and bubble through the column to exit at the top. The volatile products flash and are removed from the column via a quench condenser which incorporates inhibitor injection. The condensed liquid can then be sent to a second column where the methyl acrylate and acetic acid are taken overhead and unreacted methyl 2-acetoxypropionate is recovered as the residue stream and recycled back to the reactor column. Some transesterification of the methyl acrylate and acetic acid to acrylic acid and methyl acetate may or may not also take place, depending on the high boiling liquid.

Figure 3:
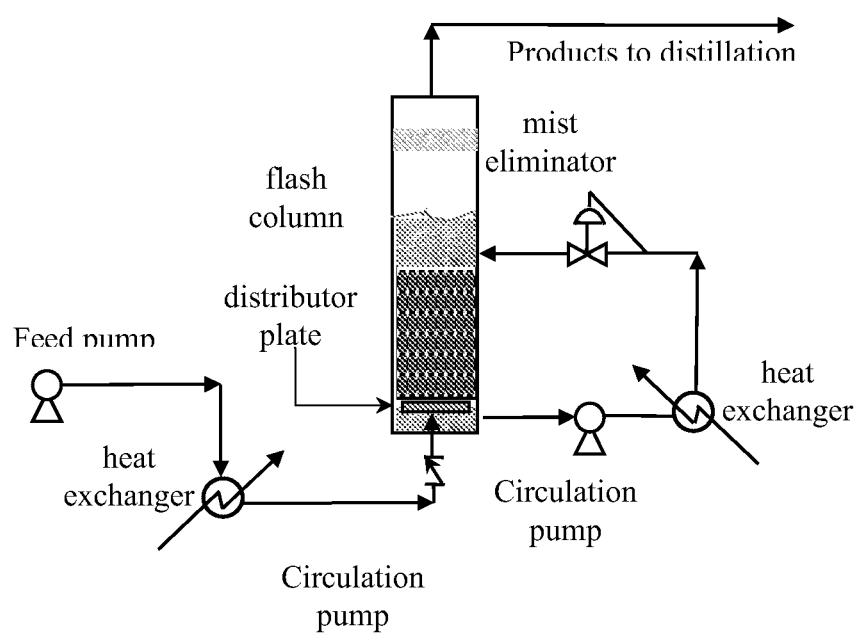

As an alternative, the reactor may also be filled with a solid packing to increase mass transfer and enhance the reaction rate. This is shown in FIG. 3 below. These solids could also be or contain compounds which act as heterogeneous catalyst for the cracking. Some examples of the heterogeneous catalyst are calcium sulfate, calcium monohydrogen phosphate, acid washed carbon granules, acidic zeolites, acidic clays, silica, etc.

The high boiling liquid can be any liquid which boils at temperatures above about 250° C. and is thermally stable. Examples of the high boiling liquid are heat transfer liquids such as Dowtherm A, Paratherm HR, Dynalene HT, and Ucon HTF 14. The high boiling liquid may contain small amounts of a mineral acid such as phosphoric acid or sulfuric acid. These acids are present as a homogeneous catalyst for the pyrolysis reaction. Lewis acids such as zinc acetate, cupric acetate or manganese acetate could also be used catalysts. Heteropoly acids such as tungstophosphoric acid or molybdosilicic acid can also be employed as catalyst for this pyrolysis reaction. These acidic homogeneous catalysts are present in low concentrations (10-1000 ppm level) in the high boiling liquid. In fact one or more of these acidic catalysts may be present in the high boiling liquid.

Another class of high boiling liquids which can act as both reaction medium and catalyst would be ionic liquids such as:
1-butyl-3-methylimidazolium hexafluorophosphate
1-butyl-3-methylimidazolium methylsulfonate
1-ethyl-3-methylimidazolium diethylphosphate
1-ethyl-3-methylimidazolium hydrogen sulfate
4-(3-butyl)-imidazolio-1-butanesulfonate These ionic liquids could also contain low levels (10-1000 ppm) of one or more of the acidic catalysts noted above. The high boiling liquid can be a mixture of two or more ionic liquids such as:
1-butyl-3-methylimidazolium hexafluorophosphate
1-butyl-3-methylimidazolium methylsulfonate
1-ethyl-3-methylimidazolium diethylphosphate
1-ethyl-3-methylimidazolium hydrogen sulfate
4-(3-butyl)-imidazolio-1-butanesulfonate One or more phosphate esters, such as tricresyl phosphate, triphenyl phosphate or cresyl diphenyl phosphate would be other candidate high boiling liquids as well as molten monosodium phosphate. These high boiling liquids could also contain low levels (10-1000 ppm) of one or more of the acidic catalyst noted above.

Another class of liquids is eutectic salts that melt at low enough temperatures (~150° C.) to be useful in the process. Another class of liquids is eutectic metal alloys or metals that melt at low enough temperatures (~150° C.) to be useful in the process. In particular, bismuth tin alloys are of interest. These molten salts and metals may also be doped with additional materials to act as catalysts in the pyrolysis process.

This novel process allows the methyl 2-acetoxypropionate or 2-acetoxypropionic acid to be injected as a liquid and remain as a liquid until injected in the reactor, where the evaporation and thermal cracking occurs. The residence time of the gas phase in the reactor may be very short (0.1-10 second) to help prevent side reactions. Once the liquid enters the reactor the methyl 2-acetoxypropionate or 2-acetoxypropionic acid cracks into the products (i.e. methyl acrylate and acetic acid or acrylic acid and acetic acid) which flash and are separated from the high boiling liquid, again to prevent side reactions. To prevent polymerization of the acrylate products the high boiling liquid must also contain a thermally stable polymerization inhibitor such as phenothiazine or a TEMPO inhibitor such as 4-hydroxy TEMPO, 4-methoxy TEMPO or 4-acetoxy TEMPO. These inhibitors are non-volatile and remain in the high boiling liquid reboiler residue. The methyl 2-acetoxypropionate or 2-acetoxypropionic acid feed can contain a small amount of make-up inhibitor for the reboiler residue.

The reactor may also have a back pressure regulator at the exit to maintain the MAP in the liquid state to enhance the thermal cracking of the MAP. The reactor may be run under pressure. Running the reactor at a sufficiently high pressure would allow the majority of the unreacted methyl 2-acetoxypropionate or 2-acetoxypropionic acid to be retained in the reactor as liquid until it is reacted or removed as a liquid for purification and recycle.

The distillation column can be a single stage flash or contain several theoretical stages. The theoretical stages can be accomplished by either packing or trays. The overhead pressure of the column can be either atmospheric, or sub-atmospheric or super atmospheric. One possible embodiment of the invention would be a single stage flash run at atmospheric pressure. Another possible embodiment of the invention would be a multistage column with the methyl acrylate and acetic acid taken as an overhead stream and the unreacted methyl 2-acetoxypropionate taken as a liquid side stream on a tray low in the column. The unreacted methyl 2-acetoxypropionic acid is recycled to the forced circulation loop. Inhibitor must be added in the reflux to the column to prevent fouling on the trays. A preferred method of addition is to utilize a quench condenser and add the inhibitor solution to the cooled pump around spray of the condenser. The preferred inhibitor would be either phenothiazine or a TEMPO inhibitor, such as 4-hydroxy TEMPO, 4-acetoxy TEMPO or 4-methoxy TEMPO.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification The invention is demonstrated by but not limited by the following examples:

EXAMPLE 1

A 300 mL autoclave was charged with 150 g of methyl acetate, 6 g lactide and 0.2 g of solid sodium methoxide. The contents were heated and stirred at 200° C. for 24 hrs. The contents were cooled and then analyzed by GC revealing 3.3 area percent methyl 2-acetoxypropionate and 0.02 area percent lactide.

EXAMPLE 2

A 300 mL autoclave was charged with 150 g of methyl acetate, 6 g lactide and 0.2 g of solid potassium hydroxide. The contents were heated and stirred at 200° C. for 24 hrs. The contents were cooled and then analyzed by GC revealing 2.9 area percent methyl 2-acetoxypropionate and 0.05 area percent lactide.

EXAMPLE 3

A 300 mL autoclave was charged with 150 g of methyl acetate, 6 g lactide and 0.2 g of solid sodium acetate. The contents were heated and stirred at 200° C. for 24 hrs. The contents were cooled and then analyzed by GC revealing 1.4 area percent methyl 2-acetoxypropionate and 0.3 area percent lactide.

EXAMPLE 4

A 300 mL autoclave was charged with 150 g of methyl acetate, 6 g lactide and 0.2 g of solid potassium acetate. The contents were heated and stirred at 200° C. for 24 hrs. The contents were cooled and then analyzed by GC revealing 1.4 area percent methyl 2-acetoxypropionate and 0.3 area percent lactide.

EXAMPLE 5

A 300 mL autoclave was charged with 150 g of methyl acetate, 6 g lactide and 0.2 g of solid sodium acetate. The contents were heated and stirred at 240° C. for 24 hrs. The contents were cooled and then analyzed by GC revealing 2.5 area percent methyl 2-acetoxypropionate and 0.1 area percent lactide.

EXAMPLE 6

A 250 mL round bottom flask was charged with 43 g methyl acrylate, 30 g acetic acid, 5 g Purolite PD206 sulfonic acid resin, 0.03 g of 4-hydroxy TEMPO and 0.01 g nitrosobenzene. The flask was fitted with a reflux condenser, a heating mantel and a magnetic stirrer. The contents were held at ~85° C. for 6 hrs. At the end of the 6 hrs, GC analysis revealed that the flask contained; 36.4% methyl acrylate, 25.4% acetic acid, 17.5% methyl acetate and 19.3% acrylic acid.

EXAMPLE 7

Methyl acetoxy propionate (MAP) was dissolved to about 5% in 95% acetonitrile and 0.5 microliters of the resulting solution was injected into the inlet of an HP 5890 GC at 325° C. The column was a 30M×0.32 mm×0.25 μm HP Innowax column. The inlet contained approximately 0.5 g of calcium sulfate. The MAP was cracked in the inlet, forming methyl acrylate and acrylic acid together with methyl acetate and acetic acid, with some remaining MAP. The response factors of the various compounds were not determined, so a material balance was not calculated. Based on the area counts, the conversion of the MAP was about 85%. The methyl acrylate plus acetic acid accounted for about 54% of the reacted MAP, and the acrylic acid plus methyl acetate accounted for about 42% of the reacted MAP.

EXAMPLE 8

Methyl acetoxy propionate (MAP) was dissolved to about 50% in acetic acid and 0.5 microliters of the resulting solution was injected into the inlet of an HP 5890 GC at 325° C. The column was a 30M×0.32 mm×0.25 μm HP Innowax column. The inlet contained approximately 0.5 g of calcium sulfate. The MAP was cracked in the inlet, forming methyl acrylate and acrylic acid together with methyl acetate and acetic acid, with some remaining MAP. The response factors of the various compounds were not determined, so a material balance was not calculated. Based on the area counts, the conversion of the MAP was less than 40%.

The invention claimed is:
1. A process for the production of acrylic acid comprising the following steps: a) reacting methyl acetate with a lactic acid molecular complex to produce methyl 2-acetoxypropionate in the presence of a base catalyst; b) pyrolyzing methyl 2-acetoxypropionate to methyl acrylate and acetic acid; c) transesterifying in a reactor the methyl acrylate and acetic acid to a mixture of methyl acrylate, acetic acid, methyl acetate and acrylic acid with a catalyst; d) separating the methyl acetate for recycle to a methyl 2-acetoxypropionate reactor; e) separating the acrylic acid for further refining; and f) separating the mixture of methyl acrylate and acetic acid for recycle to a transesterification reactor.

2. The process for the production of acrylic acid of claim 1, wherein the base catalyst is an alkali base selected from the group consisting of: alkali methoxide, alkali hydroxide, alkali acetate, sodium methoxide, sodium hydroxide, sodium acetate, potassium methoxide, potassium hydroxide, potassium acetate, and combinations thereof.

3. The process for the production of acrylic acid of claim 1 wherein the catalyst set out in step (c) is selected from the group consisting of: a mineral acid, a solid acid, an organic sulfonic acid, and combinations thereof.

4. The process for the production of acrylic acid of claim 1 wherein the catalyst set out in step (c) is selected from the group consisting of sulfuric acid, phosphoric acid, strong acid resin, methane sulfonic acid, dodecylbenzene sulfonic acid, and combinations thereof.

5. The process for the production of acrylic acid of claim 1 wherein the catalyst set out in step (c) is selected from the group consisting of: Amberlyst 30, Marathon C, and combinations thereof.

6. The process for the production of acrylic acid of claim 1 wherein the lactic acid molecular complex is lactide.

7. The process for the production of acrylic acid of claim 1 further comprising the step of purifying the acrylic acid from step (e) into glacial acrylic acid by melt crystallization.

8. The process of claim 1 further comprising the step of converting the acrylic acid into an acrylate ester by reacting the acrylic acid with a C-1 to C-8 alcohol.

9. The process for the production of acrylic acid of claim 1 in which the step of pyrolizing methyl 2-acetoxypropionate to methyl acrylate and acetic acid occurs in the presence of a catalyst selected from the group consisting of: calcium sulfate; a zeolite; mesoporous molecular sieves; naturally occurring acidic clays; acidic metal oxides; acidic non-metal oxides; acidic doped metal oxides; Lewis acids; transition metal salt of a mineral acid; hetero-poly acids; and combinations thereof.

10. The process for the production of acrylic acid of claim 9 in which the catalyst of the pyrolizing step is supported on a structure selected from the group consisting of:
 a. a monolithic structure with a multiplicity of internal channels for gas flow and surface reaction, with the active catalytic material washcoated on the internal surfaces of the monolith,
 b. a structured packing with the active catalytic material supported on the surface of the packing, and
 c. a monolithic structure, with the active catalytic material on the surfaces of the monolithic structure by solution impregnation.

11. The process for the production of acrylic acid of claim 9 wherein the catalyst used in the step of pyrolizing methyl 2-acetoxypropionate to methyl acrylate and acetic acid is selected from the group consisting of: ultrastable y-type zeolite, mordenite, Hydrophobic Zeoloite Socony Mobil number 5, X zeolite, beta zeolite, Sn-beta zeolite, Mobil Composition of Matter number 41, montmorillonite clay, kaolinite clay, alumina, tin (IV) oxide, molybdenum oxide, silica, phosphorous pentoxide, sulfated zirconia, tungstated zirconia, sulfonated silica, tungstated tin oxide, W—Nb mixed-oxides, $FeCl_3$, $AlCl_3$, $ScCl_3$, Tungstosilicic acid, Molybdosilicic acid, Tungstophosphoric acid, Molybdophosphoric acid, and combinations thereof.

12. The process for the production of acrylic acid of claim 9 in which the catalyst of the pyrolizing step is formed as a pelleted material.

\* \* \* \* \*